United States Patent [19]
Kopito et al.

[11] 4,002,056
[45] Jan. 11, 1977

[54] PROCESSES AND DEVICES FOR DETERMINING PROPERTIES OF VISCOUS FLUIDS

[75] Inventors: Louis Kopito, Brookline; Samuel R. Schuster, Wellesley; Harold Kosasky, Brookline, all of Mass.

[73] Assignee: Ovutime, Inc., Brookline, Mass.

[22] Filed: Dec. 4, 1975

[21] Appl. No.: 637,830

Related U.S. Application Data

[63] Continuation-in-part of Ser. No. 558,247, March 14, 1975, Pat. No. 3,926,037.

[52] U.S. Cl. .................................. 73/53; 23/230 B; 73/64.4
[51] Int. Cl.[2] .................. G01N 33/16; G01N 13/02
[58] Field of Search ................ 73/58, 53, 60, 64.4, 73/9, 10, 169, 150 A, 150 R, 141 AB; 128/2 W; 23/230 B

[56] References Cited

UNITED STATES PATENTS

| | | | |
|---|---|---|---|
| 2,756,587 | 7/1956 | Doble | 73/64.4 |
| 3,036,459 | 5/1962 | Kendall | 73/141 AB X |
| 3,463,014 | 8/1969 | Katz et al. | 73/169 |

FOREIGN PATENTS OR APPLICATIONS

733,686   7/1932   France .................................. 73/169

*Primary Examiner*—Richard C. Queisser
*Assistant Examiner*—Joseph W. Roskos
*Attorney, Agent, or Firm*—Morse, Altman, Oates & Bello

[57] ABSTRACT

A device for determining the rheological properties of a fluid comprises a pair of cooperating members, the working face of each member defining parallel discrete ridges or flutes, the outermost portions of which define ridge lines, the ridges of one member being crossed with respect to the ridges of the other member. A fluid sample is applied to the working face of one member and the working faces are pressed together so that the ridge lines of one member intersect the ridge lines of the other member at a matrix of points and so that volume increments of the fluid sample are defined. The contact surface area of the fluid sample with the substrate is substantially greater than the surface area of the general interface between the working faces. The force required to separate the fluid at the general interface defines the rheological properties of the fluid with improved accuracy.

12 Claims, 7 Drawing Figures

PROCESSES AND DEVICES FOR DETERMINING PROPERTIES OF VISCOUS FLUIDS

RELATED APPLICATION

The present application is a continuation-in-part of co-pending application Ser. No. 558,247, filed Mar. 14, 1975 and now U.S. Pat. No. 3,926,037.

BACKGROUND OF THE INVENTION

1. Field of the Invention

The invention relates to processes and devices for determining physical properties of fluids and, more particularly, is directed toward processes and devices for determining the rheological properties of fluids.

2. Description of the Prior Art

Various instruments have been proposed for testing certain viscoelastic properties of fluids including adhesion, cohesion, surface tension, viscosity, and yield stress. One example of such instruments involves relatively rotatable elements having bearing surfaces between which a fluid to be tested is placed. Another example of such instruments involves relatively reciprocable elements having separable bearing surfaces between which a fluid to be tested is placed. In each case, the associated elements are biased to provide a mechanically related indicium of the properties of the fluid between them. One of the major difficulties encountered in the measurement of the viscoelastic properties of fluids other than "ideal" or Newtonian fluids is that the properties being measured may be altered during the act of measurement. Rotational viscometers tend to homogenize the specimens by the act of shearing the sample between the two rotating surfaces. Capillary devices similarly destroy some viscoelastic properties by shearing and by surface tension between the inner wall of the capillary and the fluid being measured. Fluids, which contain substantial solids, i.e. the dry residue after evaporation of the liquid, such as milk, cream, ketchup, mustard, blood, etc. are composed of complex macro molecules, cross linked or other polymers, oriented or random ultrastructures, all of which contribute to their viscoelastic and other physical properties. If subjected to testing for a sufficiently long time, these fluids homogenize during testing and lose their initial characteristics. Such difficulties tend to prevent achieving a high degree of accuracy because the precise physical and geometrical condition of the fluid sample is difficult to predetermine.

SUMMARY OF THE INVENTION

It is an object of the present invention to provide processes and devices for determining the viscoelastic properties of a fluid. In accordance with the present invention, one such device comprises a pair of cooperating members, each member defining parallel, spaced ridges and troughs, the outermost portions of the ridges of which define ridge lines and the ridge lines of one member being crossed with respect to the ridge lines of the other member. When the members are pressed together with a sample fluid therebetween, the ridges of one member contact the ridges of the other member at a matrix of points so that precisely predetermined volumetric increments of the fluid sample are defined in the regions presented by the troughs. The arrangement is such as to provide the necessary prerequisites for precise measurement, namely, reproducible sample volume and thickness while controlling sample composition. The point contacts between the members eliminate prior extended area contact which introduces the undesirable variable of surface tension between flat surfaces. Sample thickness (hence sample volume) is predetermined by the design configurations of the mating ridges, by which even slight pressure of the members into their matrix point contact causes excess sample fluid to be extruded and a reproducible sample volume to be defined. The surface area of the fluid sample containing regions is substantially greater than the surface area between the working faces. The rheological measurement performed when the members are pulled apart, i.e. when the entrained specimen is torn apart, relates to the "yield point" or "shear stress" of the fluid sample. This measurement is performed instantaneously when sufficient separating force is applied in such a way as not to alter the fluid sample's viscoelastic properties.

Other objects of the present invention will in part be obvious and will in part appear hereinafter.

The invention accordingly comprises the apparatuses, processes and products, together with their parts, steps, elements and interrelationships, that are exemplified in the following disclosure, the scope of which will be indicated in the appended claims.

BRIEF DESCRIPTION OF THE DRAWINGS

A fuller understanding of the nature and objects of the present invention will become apparent upon consideration of the following detailed description taken in connection with the accompanying drawings, wherein.

DETAILED DESCRIPTION OF THE PREFERRED EMBODIMENTS

Figure 1:
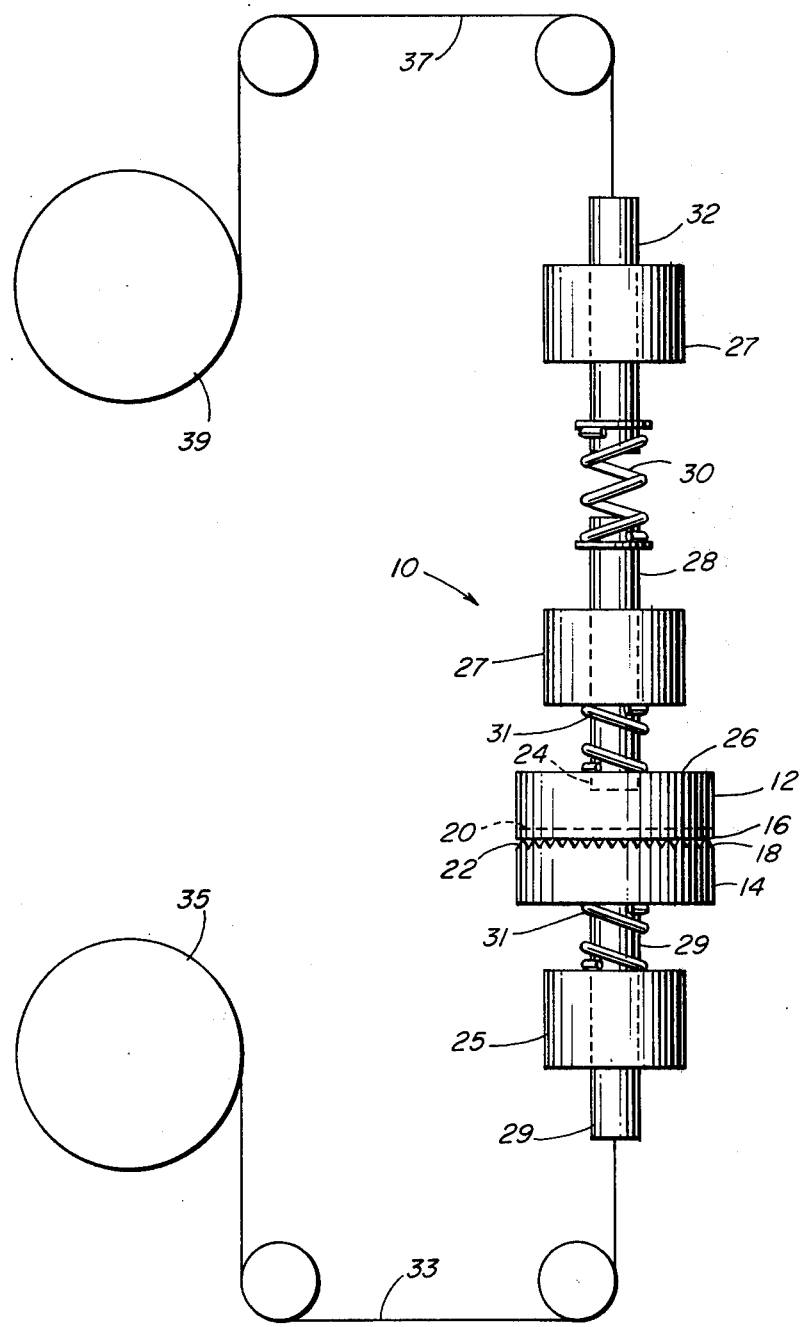
FIG. 1 is a front elevation of a device embodying the invention for determining the properties of a fluid sample.
Figure 2:
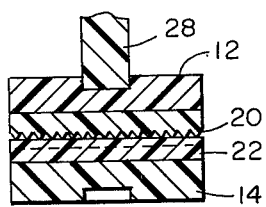
FIG. 2 is a sectional view taken axially along the device of FIG. 1.
Figure 3:
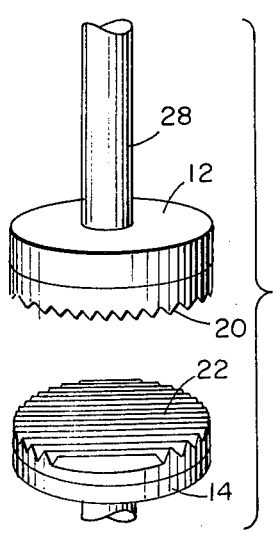
FIG. 3 is a perspective view of components of the device of FIG. 1.

Referring now to the drawings, particularly FIGS. 1, 2 and 3, there is shown one embodiment of the invention in the form of a device 10 comprising a pair of separable cooperating members 12 and 14 having working faces 16 and 18, respectively. Members 12 and 14 are composed of a dimensionally stable material, for example a vitreous material such as glass, a plastic such as methyl methacrylate, or a metallic material such as stainless steel. Each working face defines a bearing surface of predetermined surface characteristics having troughs and ridges of triangular or other cross section, the average valley to peak height being in the range of 0.001 to 5.0 mm. Such a surface, in various embodiments, is characterized by a predetermined depth and is provided by precision casting, machining, hot pressing or etching regularly spaced troughs and ridges, the outermost area of the ridges being non-planar, i.e. being sharp or rounded. In cross section, these spaced valleys and peaks take the form of elongated increments which extend outwardly to ridge lines. In the illustrated embodiment, by way of example, the predetermined surface of bearing surface 16, which is disposed at the lower face of member 12, is in the form of a plurality elongated members 20 that are in spaced parallel relationship with one another, each elongated member 20 having a triangular cross-section profile occurring at a rate of 5 to 5000 cycles per cm. In the illustrated embodiment, by way of example, the predetermined surface of bearing surface 18, which is disposed at the upper face of member 14, is in the form of a plurality of elongated members 22 that are in spaced parallel relationship with one another, each elongated member 22 having a triangular cross-sectional profile occurring at a rate of 5 to 5000 cycles per cm.

Member 12, which in the illustrated embodiment has a circular (or square or rectangular) profile having a diameter in the range of 0.5 to 4.0 cm, is formed with an axial opening 24 at an upper face 26. One end of a rod 28 is pressed or threaded into opening 24, rod 28 projecting outwardly from and in perpendicular relationship with face 26. One end of a resilient element 30, for example a spring, is secured to the free end of rod 28. The other end of spring 30 is fastened to a rod 32, which is coaxial with rod 28. Rods 28 and 32 are composed of a suitable plastic such as methyl methacrylate or polycarbonate. Elements 12, 14 are constrained for reciprocal motion toward and away from each other by a pair of slide bearings 25, 27, which receive rod 28 and a rod 29 extending from member 14 in the manner that rod 28 extends from member 12. In operation, elements 12, 14 initially are biased toward each other by springs 31, 31 with a fluid sample at the interface. Rod 29 is connected by a tension line 33 to a memory torque meter 35. Rod 37 is connected by a tension line 37 to a synchronous motor 39 having the characteristics of constant torque at constant or variable speed. The bias applied typically ranges from 0.1 to 1000 grams and is related to the size and configuration of members 12 and 14. The profile of member 14 conforms substantially to the profile of member 12.

Figure 4:
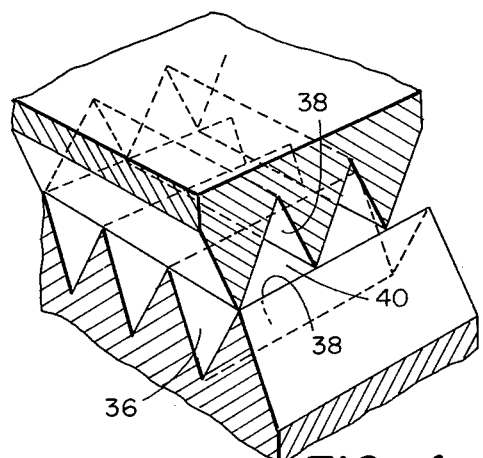
FIG. 4 is a perspective, somewhat exaggerated, view of the mating surfaces.

One process of the present invention, hereinafter described, involves the use of device 10 for determining the properties of a fluid. First, a sample of fluid is obtained by inserting member 12 into the fluid or by placing a sample between the surfaces. Next, member 12 is removed from the fluid, a sample of fluid being contained on bearing surface 16. Next, immediately after removal of member 12, bearing surface 16 is placed on and pressed against bearing surface 18, whereby the fluid is spread on the bearing surfaces. Bearing surface 16 is placed on bearing surface 18 in such a manner that the longitudinal axis of each elongated member 20 is disposed in substantially perpendicular relationship with respect to the longitudinal axis of each elongated member 22. When members 12 and 14 are pressed together, a plurality of fluid containing regions 36 are formed therebetween, one of such regions being shown in FIG. 4, somewhat exaggerated. The surface area of each fluid containing regions is substantially greater than the surface area of the interface between the bearing surfaces, the surfaces of region 36 being denoted by reference character 38 and the interface being denoted by reference character 40. When the bearing surfaces are pressed together, the fluid sample is spread to the boundary surfaces of regions 36 and excess flows out of the extremities of the troughs, the bearing surfaces being operative to provide an even thickness of the spread fluid. Next, synchronous motor 39 pulls upwardly on tension line 37 or in a direction that is substantially perpendicular to the plane of the interface between members 12 and 14. The more viscous the fluid, the greater the force necessary to pull the elements apart. Spring 30 is operative to prevent shock loading during mating of the members 12 and 14 and during separation of the members.

Figure 5:
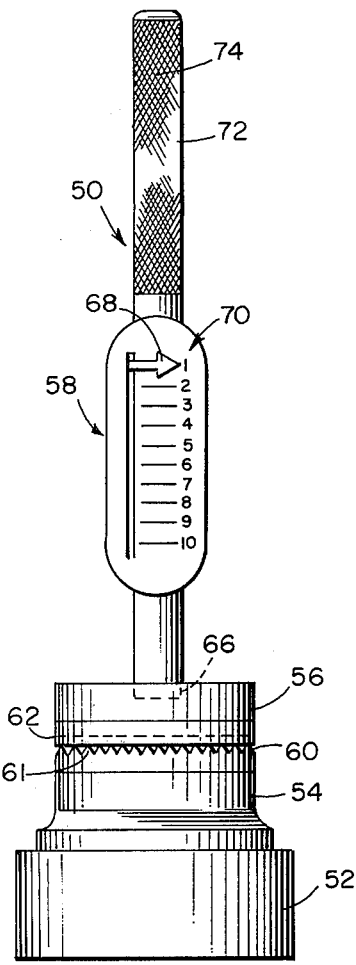
FIG. 5 is front elevation of an alternate embodiment of the invention.

Referring now to FIG. 5, there is shown an alternate embodiment of the invention in the form of a device 50. Generally, device 50 comprises a base 52 in which a lower bearing member 54 is mounted. An upper bearing member 56, which carries a force measuring device 58, rests on lower bearing member 54. Upper bearing member 56 and lower bearing memnber 54 define a pair of separable cooperating bearing members. Lower bearing member 54 includes a bearing surface 60 of predetermined surface design having valleys and ridges, the average valley ridge height being in the range of 0.001 to 5.0 mm. Such a surface, in various embodiments, is provided by machining or etching elongated parallel valleys and ridges, the ridges being sharp or rounded but in any event having ridge lines that, when crossed, intersect at a matrix of points. In cross-section, these spaced valleys and ridges take the form of prismatic facets, convoluted regular geometric shapes and the like. In the illustrated embodiment, by way of example, the predetermined surface 60 is in the form of a plurality of elongated members 61 that are in spaced parallel relationship with one another, each elongated member having a triangular cross-sectional profile occurring at a rate of 1 to 5000 cycles per cm.

Upper bearing members 56 includes a bearing surface 62 of predetermined surface characteristics having valleys and peaks, the average valley to peak height being in the range of 0.001 to 5.0 mm. Such surface configurations, in various embodiments, are provided by machining or etching regularly spaced valleys and peaks of the type above described. In the illustrated embodiment, by way of example, the predetermined surface configuration of bearing surface 62 is similar to the predetermined surface configuration of bearing surface 60, both bearing surfaces lying in substantially horizontal planes. Bearing surface 60 and 62 are characterized by like profiles, for example a circular profile having a diameter in the range of 0.5 to 4.0 cm.

Force measuring device 58, for example a spring scale, is mounted to upper bearing member 56 by means of a rod 64, which is pressed or threaded into an axial opening 66 formed in the upper bearing member. Spring scale 58 is provided with an indicator 68 that points towards indicia 70, for example a scale having the numerals 1 to 10. A rod 72 is mounted to spring scale 58 at an upper end thereof, rod 72 defining a grip for applying an upwardly directed force. The surface of rod 72 is roughened or knurled as shown at 74.

Figure 6:
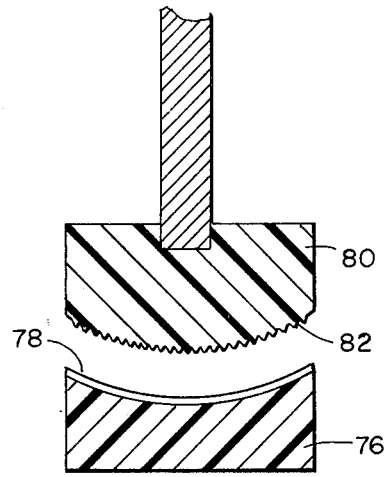
FIG. 6 is a sectional view of another alternate embodiment of the invention.
Figure 7:
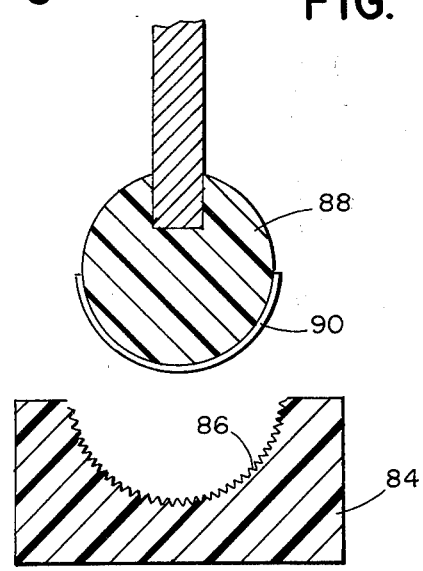
FIG. 7 is a sectional view of yet another embodiment of the invention.

Alternative bearing member configurations are shown in FIGS. 6 and 7. FIG. 6 depicts a lower bearing member 76 having a generally concave bearing surface 78 and an upper bearing member 80 having a generally convex bearing surface 82 that is adapted for interaction with bearing surface 78. Lower bearing member 76 and upper bearing member 80 define a pair of separable cooperating bearing members. Each bearing surface has a predetermined configuration that is provided by machining or etching valleys and peaks of the type above described. The average valley to peak height is in the range of 0.002 to 2.0 mm.

FIG. 7 shows a lower bearing member 84 having a hemispherical bearing surface 86 and an upper spherical bearing member 88 having a generally hemispherical bearing surface 90 that is adapted for interaction with bearing surface 86. The spacing or tolerance between bearing surfaces 82 and 86 ranges from 0.001 to 2.0 mm and preferably from 0.1 to 0.5 mm. Lower bearing member 84 and upper bearing member 88 define a pair of separable cooperating bearing members. Each bearing surface has a predetermined finish of the type described in connection with bearing surfaces 78 and 82. Preferably, each bearing member 76, 80, 84 and 88 is composed of a dimensionally stable, sterilizable material, for example, a vitreous material such as glass, a metallic material such as stainless steel, or a plastic material such as methyl methacrylate. The bearing members shown in FIGS. 6 and 7 are interchangeable with the bearing members shown in FIGS. 1 and 5, the processes described for devices 10 and 50 being applicable when the bearing members of FIGS. 6 and 7 are used.

In accordance with the present invention, each of the parallel ridges on both bearing members presents a line at its apex so that the crossed parallel ridges contact each other only at spaced points. Because contact is restricted to points and the fluid is under pressure when the bearing members are biased toward each other, the surface tension of the fluid at these points is overcome so that the distance between the bearing members is precisely predetermined.

Since certain changes may be made in the foregoing disclosure without departing from the scope of the invention herein involved, it is intended that all matter contained in the above description and shown in the accompanying drawings be construed in an illustrative and not in a limiting sense.

What is claimed is:

1. A device for determining the properties of bodily mucus comprising:
   a. a pair of separable cooperating members, each said member having a working face defining a bearing surface characterized by non-planar elongated ridge increments characterized by ridge lines, said bearing surfaces in face to face relationship define a plurality of regions adapted to contain a fluid sample, said ridge lines of one of the bearing surfaces being crossed with respect to said ridge lines of the other of the bearing surfaces to intersect in a matrix of points, the surface area of said regions being greater that the surface area of the interface between said bearing surfaces; and
   b. indicating means operatively connected to at least one of said members for providing an indication of the force required to separate said members when said regions contain a fluid sample, the force required to separate said fluid sample at said interface defining the viscoelastic properties of said fluid.

2. The device of claim 1 wherein the speed at which said force is applied indicates rate of sheer.

3. The device as claimed in claim 1 wherein the predetermined finish of each said bearing surface includes peaks and valleys, the average peak to valley height being in the range of 0.001 to 5.0 mm.

4. The device as claimed in claim 1 wherein said predetermined surface configuration of each said bearing surface is in the form of a plurality of elongated members in spaced parallel relationship to one another, each said elongated member having a substantially triangular profile in right cross-section occurring at a rate of 5 to 5000 cycles per cm.

5. The device as claimed in claim 1 wherein said indicating means includes a gravitational load operatively connected to one of said members, said gravitational load having a weight in the range of 1 to 5000 grams.

6. The device as claimed in claim 1 wherein said indicating means includes a force measuring device operatively connected to one of said members, said force measuring having indicia defining a scale.

7. A process for determining the properties of a fluid, said process comprising the steps of:
   a. placing the fluid in contact with at least one of a pair of separable cooperating members, each of said separable cooperating members having a plurality of sharp ridges, the ridges of one of said cooperating members being crossed with respect to the ridges of the other of said pair of cooperating members;
   b. pressing said cooperating members together to form a plurality of fluid containing regions, the surface area of said fluid containing regions being greater that said surface area of an interface between said cooperating members;
   c. applying a force to at least one of said cooperating members, said force tending to cause relative motion of said cooperating members with respect to each other; and
   d. indicating the occurrence of said relative motion for determining the properties of said fluid.

8. The process as claimed in claim 7 wherein each said cooperating member has a working face defining a bearing surface of predetermined finish to form said plurality of fluid containing regions when said cooperating members are pressed together.

9. The process as claimed in claim 7 wherein each of said bearing surfaces is formed with peaks and valleys, the average peak to valley height being in the range of 0.0002 to 2.0 mm.

10. The process as claimed in claim 7 wherein said force applying step includes the step of lifting one of said cooperating members, a gravitational load having a weight in the range of 10 to 1000 grams being connected to the other of said cooperating members.

11. The process as claimed in claim 7 wherein said force applying step includes the step of lifting at constant rate one of said cooperating members, the other of said cooperating members being fixed against movement, the occurrence of relative motion being indicated on a force measuring device operatively connected to said one cooperating member.

12. The process as claimed in claim 7 wherein said force applying step includes the step of lifting at variable rate one of said cooperating members, the other of said cooperating members being fixed against movement, the occurrence of relative motion being indicated on a force measuring device operatively connected to said one cooperating member.

* * * * *